United States Patent [19]
Omietanski et al.

[11] 3,933,695
[45] Jan. 20, 1976

[54] HYDROXYALKENYLSILOXANE RIGID POLY URETHANE FOAM STABILIZERS

[75] Inventors: George M. Omietanski; Vincent T. Chuang, both of Marietta, Ohio

[73] Assignee: Union Carbide Corporation, New York, N.Y.

[22] Filed: July 17, 1974

[21] Appl. No.: 489,125

Related U.S. Application Data

[62] Division of Ser. No. 319,786, Dec. 29, 1972, Pat. No. 3,842,112.

[52] U.S. Cl............................ 260/2.5 AH; 252/352
[51] Int. Cl.$^2$......................................... C08G 18/14
[58] Field of Search................ 260/2.5 AH; 252/352

[56] References Cited
UNITED STATES PATENTS

| | | | |
|---|---|---|---|
| 2,823,218 | 2/1958 | Speier et al.................. | 260/448.2 E |
| 2,837,550 | 6/1958 | Prober......................... | 260/448.2 B |
| 2,920,093 | 1/1960 | Bailey.......................... | 260/448.2 Q |
| 2,970,150 | 1/1961 | Bailey.......................... | 260/448.2 E |
| 3,317,460 | 5/1967 | Clark et al. ................ | 260/448.2 B X |

*Primary Examiner*—H. S. Cockeram
*Attorney, Agent, or Firm*—Eugene C. Trautlein

[57] ABSTRACT

This application relates to certain novel hydroxyalkenylsiloxanes that are particularly useful as foam stabilizers for rigid polyurethane foams. The novel hydroxyalkenylsiloxanes have critical siloxane molecular weights and are produced by an addition reaction involving hydrosiloxanes and acetylenically unsaturated alcohols that contain a terminal acetylenic bond which does not shift significantly during the reaction.

3 Claims, No Drawings

HYDROXYALKENYLSILOXANE RIGID POLYURETHANE FOAM STABILIZERS

CROSS REFERENCES TO RELATED APPLICATION

This application is a division of U.S. Pat. application Ser. No. 319,786, filed Dec. 29, 1972 now U.S. Pat. No. 3,842,112.

Rigid polyether polyurethane foams are produced commercially by introducing several starting materials (i.e., a silicone surfactant, a polyether polyol, a fluorocarbon blowing agent, a catalyst and a polyisocyanate) into a reaction zone. It is important that the relative amounts of the materials in the reaction zone be carefully controlled in order to produce a satisfactory polyurethane foam. Control of the relative amount of the starting materials in the reaction zone is achieved, in part, by forming premixtures containing carefully controlled amounts of the silicone surfactant (i.e., a siloxane-polyoxyalkylene block copolymer), polyol, and fluorocarbon. It is desirable that the various components in these premixtures be compatible so as to eliminate the need for stirring the premixtures to insure homogeneity. Certain silicone surfactants are more compatible with the other starting materials in the premixtures than are other silicone surfactants. In particular, those silicone surfactants wherein the polyoxyalkylene blocks are endblocked by hydroxyl groups are generally more compatible in premixtures than are silicone surfactants wherein the polyoxyalkylene blocks are endblocked by alkoxy groups.

Siloxane-polyoxyalkylene block copolymers wherein the polyoxyalkylene blocks are endblocked by hydroxyl groups are often prepared by the addition of a linear polyoxyalkylene polymer endblocked at one end by an allyl group and at the other end by a hydroxyl group (or a group convertible to a hydroxyl group) with a hydrosiloxane. Such polyoxyalkylene reactants can be produced by reacting allyl alcohol with one or more alkylene oxides followed, if desired, by converting the hydroxy group to a group convertible to a hydroxyl group. In the addition reaction, the SiH groups add to the allyl group to produce the block copolymer. When the polyoxyalkylene reactant contains an alcoholic hydroxyl endblocking group, such groups can also react to some extent with SiH groups thereby decreasing the content of the desired hydroxyl groups in the block copolymer product with a resulting decrease in the compatibility of the block copolymer in the above-mentioned premixtures. This side reaction also undesirably increases the viscosity of the block copolymer product by partially crosslinking the block copolymer. Further, during the addition reaction, endblocking allyl groups in the polyoxyalkylene reactant tend to isomerize to some extent to propenyl groups which can react with the hydroxyl endblocking groups of the polyoxyalkylene reactant or block copolymer to form acetal groups. These side reactions also reduce the premixture compatability of the block copolymer by decreasing its hydroxyl content and also lead to an undesirable viscosity increase in the block copolymer by partially crosslinking the block copolymer.

When the polyoxyalkylene reactant contains an endblocking group convertible to a hydroxyl group, the undesirable side reactions of the hydroxyl group with the SiH groups and propenyl groups do not occur but the undesirable isomerization of allyl groups can still occur and the block copolymer initially formed must be further processed to regenerate the hydroxyl groups.

It is an object of this invention to provide hydroxyalkylsiloxanes that are useful as foam stabilizers for rigid polyether polyurethane foams.

It is an object of this invention to provide hydroxyalkylsiloxanes that are useful as foam stabilizers for rigid polyether polyurethane foams and that are readily produced from relatively simple alcohol reactants.

It is an object of this invention to provide hydroxyalkylsiloxanes that are useful as foam stabilizers for rigid polyether polyurethane foams and that are produced by a process relatively free of undesirable side reactions.

Other objects of this invention will be apparent from the description thereof appearing below.

This invention provides hydroxyalkenylsiloxanes consisting essentially of: (A) at least one hydroxyalkenylsiloxane unit having the formula:

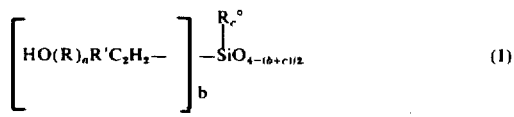 (I)

wherein R is a divalent hydrocarbon group free of aliphatic carbon to carbon multiple bonds, R' is an arylene group, a cycloalkylene group that has no hydrogen bonded to the carbon atom attached to the $C_2H_2$ group and that is free of aliphatic carbon to carbon multiple bonds or a divalent- $CR''_2$-group, R'' and R° are each monovalent hydrocarbon groups free of aliphatic carbon to carbon multiple bonds and having from 1 to 10 inclusive carbon atoms, $C_2H_2$ is a —CH=CH— or a

group, each hydroxyalkenylsiloxane group has no more than 20 (preferably no more than 10) carbon atoms, a has a value of 0 or 1, b has a value of 1, 2 or 3, c has a value of 0, 1 or 2, and (b+c) has a value of 1, 2 or 3; and (B) at least three hydrocarbylsiloxane units represented by the formula:

 (II)

wherein $R^\infty$ is a monovalent hydrocarbon group free of aliphatic carbon to carbon multiple bonds and having from 1 to 10 inclusive carbon atoms and d has a value of 1, 2 or 3, the molecular weight of the siloxane portion of the hydroxyalkenylsiloxane being from about 250 to about 1300 inclusive, and, when dihydrocarbylsiloxane units ($R_2^\infty SiO$ units) are present, the ratio of hydroxalkenylsiloxane units to dihydrocarbylsiloxane units is at least 0.5 to 1.0. Those of the hydroxyalkenylsiloxanes of this invention containing at least one hydroxyalkenylsiloxane unit represented by formula (I) above wherein b+c is 1 or 2 are stable in premixtures containing the siloxane, a polyol and a blowing agent and so such siloxanes are preferred. Preferably, the siloxane portion represents from 60 to 80 weight percent of the hydroxyalkenylsiloxane and the hydroxyalkenylsiloxane has a viscosity up to 5000 centistokes at 25°C. As used herein, the "siloxane portion" of the hydroxyalkenylsiloxane includes all of the groups and atoms in the hydroxyalkenylsiloxane apart from the hydroxyalkenyl groups, i.e., apart from the HO(R)$_n$R'CH=CH- groups.

A preferred class of the hydroxyalkenylsiloxanes of this invention are represented by the average formula:

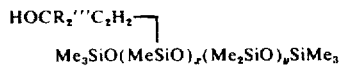

Me$_3$SiO(MeSiO)$_x$(Me$_2$SiO)$_y$SiMe$_3$      (III)

wherein R''' is a methyl or ethyl group, Me is a methyl group, x has a value from 1 to 8 inclusive, y has a value from 1 to 6 inclusive, the molecular weight of the hydroxyalkenylsiloxane, exclusive of the hydroxyalkenyl groups, is from about 300 to about 1000 inclusive and x:y is at least 0.5:1.

Typical of the monovalent hydrocarbon groups free of aliphatic carbon to carbon multiple bonds represented by R°, R'', R''' and R$^\infty$ in formulas (I), (II) and (III) above are the alkyl groups (for example the methyl, ethyl, n-propyl, iso-propyl, n-butyl, sec-butyl, isobutyl, t-butyl, n-octyl and decyl, groups), the cycloalky groups (for example, the cyclopropyl, cyclobutyl, cyclopentyl, cyclohexyl, and cycloheptyl groups), the aryl groups (for example, the phenyl and naphthyl groups), the aralkyl groups (for example, the benzyl, 2-phenyl-ethyl, 2-phenylpropyl, cumyl groups), and the alkaryl groups (for example, the tolyl, t-butylphenyl and styryl groups). Typical of the divalent hydrocarbon groups represented by R in formula (I) above are the alkalkylene and arylene groups (e.g., the methylene, ethylene, propylene, cyclohexylene and phenylene groups). Typical of the cyclic divalent hydrocarbon groups free of aliphatic carbon to carbon multiple bonds represented by R' in formula (I) above are the arylene groups such as the phenylene and tolylene groups and the cycloalkylene groups such as:

This invention still further provides a process for producing the hydroxyalkenylsiloxanes described above which process comprises reacting (1) an acetylenic alcohol represented by the formula:

HO(R)$_n$R'C≡CH      (IV)

wherein the symbols are as defined for formula (I) with (2) a hydrosiloxane consisting essentially of (A) at least one siloxane unit having the formula:

wherein the symbols are as defined for formula (I), and (B) at least three units having formula (II) above, the molecular weight of the hydrosiloxane being from 250 to 1300 inclusive, in the presence of (3) a catalyst for the addition of SiH to olefinic bonds. When hydroxyalkylsiloxanes of this invention containing dihydrocarbylsiloxane units are produced, the hydrosiloxane reactant must have a ratio of hydrosiloxane units to dihydrocarbylsiloxane units of at least 0.5 to 1.

Typical of the acetylenic alcohols that are useful in producing the hydroxyalkenylsiloxanes of this invention are the following:

3-Hydroxy-3-methyl-1-butyne    HC≡CCMe$_2$OH

1-Hydroxy-1-ethynyl cyclohexane

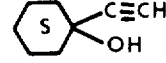

Propargyl alcohol    HC≡C—CH$_2$OH
3-Hydroxy-1-butyne    HC≡C—CMeHOH

The hydrosiloxane reactants used to produce the hydroxyalkenylsiloxanes of this invention can be produced by cohydrolyzing and cocondensing the appropriate hydrolyzable silanes or by equilibrating appropriate siloxanes using conventional techniques.

The process for producing the hydroxyhydroalkenylsiloxanes of this invention is conducted in the same manner as used in producing known hydrosiloxane-alkyne adducts (i.e., at elevated temperatures and in the presence of a catalyst). Since relatively little side reactions occur, approximately stoichiometric amounts of the olefinic alcohol and the hydrosiloxane (one acetylenic group per SiH group) can be employed. Solvents for the alcohol and hydrosiloxane reactants (e.g., liquid hydrocarbons such as toluene) can be employed. Amounts of platinum catalysts that provide from 10 to 200 parts by weight of platinum per million parts by weight of the reactants are useful. Suitable reaction temperatures are from 50°C. to 100°C. Suitable addition catalysts include chloroplatinic acid and complexes thereof and elemental platinum supported on charcoal or gamma alumina. At the conclusion of the process, any residual (unreacted) SiH can be removed by adding a small amount of methanol and sodium bicarbonate to the product and heating.

In view of the fact that the acetylenic bonds in the acetylenic alcohol reactants used in producing the siloxanes of this invention do not isomerize during the reaction with hydrosiloxanes and do not undergo other side reactions significantly, the resulting product contains little undesirable by products. Another advantage of this process is that it involves the use of monomeric alcohol reactants as distinguished from the polyoxyalkylene alcohol reactants employed in prior art processes. Further, the monomeric alcohol reactants employed in the process of this invention need not be reacted to block the hydroxy groups as is done in some prior art processes involving the use of polyoxyalkylene alcohol reactants.

This invention also provides a method for producing rigid polyurethane foams by reacting and foaming a foam formulation (reaction mixture) comprising (a) a polyether containing at least two hydroxyl group and having a hydroxyl number from about 200 to about 1000, (b) an organic polyisocyanate, (c) a catalyst for the reaction of (a) and (b) to produce the polyurethane, (d) a blowing agent and (e) a novel hydroxyalkenylsiloxane as described above as a foam stabilizer.

The polyethers that are useful in producing rigid polyurethane foam in accordance with this invention include polyoxyalkylene polyols including alkylene oxide adducts of, for example, glycerol, 1,2,6-hexanetriol, 1,1,1-trimethylolethane, 1,1,1-trimethylolpropane, pentaerythritol, sorbitol, sucrose, lactose, alpha-methylglucoside, alpha-hydroxy-alkylglucoside, ammonia, triethanolamine, triisopropanolamine, ethylenediamine, diethyylenetriamine, novolac resins, phosphoric acid, benzenephosphoric acid, polyphosphoric acids such as tripolyphosphoric acid and tetrapolyphosphoric acid, phenol-aniline-formaldehyde ternary condensation products, aniline-formaldehyde condensation products, and the like, are useful. The alkylene oxides employed in producing polyoxyalkylene polyols normally have from 2 to 4 carbon atoms. Propylene oxide and mixtures of propylene oxide with ethylene oxide are preferred.

The hydroxyl number of the polyether polyols in producing polyurethane foams in accordance with this invention can range from about 200 to about 1000. The hydroxyl number is defined as the number of milligrams of potassium hydroxide required for the complete neutralization of the hydrolysis product of the fully acetylated derivative prepared from 1 gram of polyol. The hydroxyl number can also be defined by the equation:

$$OH = \frac{56.1 \times 1000 \times f}{m.w.}$$

where
OH=hydroxyl number of the polyol
f=average functionality, that is, average number of hydroxyl groups per molecule of polyol
m.w. average molecular weight of the polyol.

The organic polyisocyanates that are useful in producing polyurethane foams in accordance with this invention are organic compounds that contain at least two isocyanato groups. Suitable organic polyisocyanates include the poly(aryleneisocyantes) and the hydrocarbon diisocyanates, (e.g., the alkylene diisocyanates and the arylene diisocyanates).

Illustrative of suitable polyisocyanates are 1,2-diisocyanatoethane, 1,3-diisocyanatopropane, 1,2-diisocyanatopropane, 1,4-diisocyanatobutane, 1,5-diisocyanatopentene, 1,6-diisocyanatohexane, bis(3-isocyanatopropyl)ether, bis(3-isocyanatopropyl)sulfide, 1,7-diisocyanatoheptane, 1,5-diisocyanato-2-dimethylpentane, 1,6-diisocyanato-3 methoxyhexane, 1,8-diisocyanatooctane, 1,5-diisocyanato-2,2,4-trimethylpentane, 1,9-diisocyanatononane, 1,10-di(isocyanatopropyl)ether of 1,4-butylene glycol, 1,11-diisocyanatoundecane, 1,12-diisocyanatododecane, bis(isocyanatohexyl)sulfide, 1,4-diisocyanatobenzene, 2,4-diisocyanatotoluene, 2,6-diisocyanatotolylene, 1,3-diisocyanato-o-xylene, 1,3-diisocyanato-m-xylene, 1,3-diisocyanato-p-xylene, 2,4-diisocyanato-1-chlorobenzene, 2,4-diisocyanato-1-nitrobenzene, and 2,5-diisocyanato-1-nitrobenzene. Suitable poly(aryleneisocyanates) include polymethylene poly(phenyleneisocyanates) having the formula:

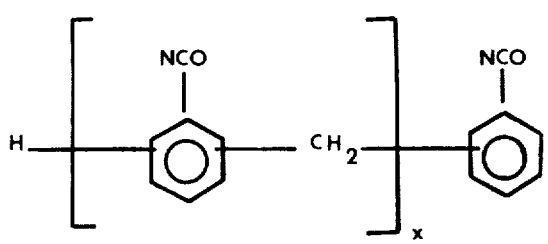

wherein x has an average value from 1.1 to 5 inclusive (preferably from 2.0 to 3.0).

The catalysts that are useful in producing polyurethane foams in accordance with this invention include amine catalysts and metal catalyst. Useful amine catalysts include tertiary amines such as N,N-dimethyl-2-[2-dimethylaminoethoxy]ethylamine, trimethylamine, N-methylmorpholine, N-ethylmorpholine, N,N-dimethylbenzylamine, N,N-dimethylethanolamine, N,N,N',-N'-tetramethyl-1,3-butanediamine, triethanolamine, 1,4-diazabicyclo[2,2,2] octane (triethylenediamine), hexadecyldimethylamine, and the like. Useful metal catalysts include dibutyl tin dilaurate.

Blowing agents that are useful in producing polyurethane foam in accordance with this invention include water, halogenated hydrocarbons (e.g., fluorocarbons) such as trichloromonofluoromethane, dichlorodifluoromethane, dichloromonofluoromethane, dichloromethane, trichloromethane, 1,1-dichloro-1-fluoroethane, 1,1,2-trichloro-1,2,2-trifluoromethane, hexafluorocyclobutane, octafluorocyclobutane, and the like. Another class of blowing agents include thermally unstable compounds which liberate gases upon heating, such as N,N'-dimethyl-N,N'-dinitrosoterephthalamide and the like.

The relative amounts of the various components used in producing polyurethane foams in accordance with this invention are not narrowly critical. The polyether polyol and the polyisocyanate, taken together, are present in the foam formulations (reaction mixtures) used to produce such foams in a major amount. The relative amounts of these two components is the amount required to produce a polyurethane structure of the foam and such relative amounts are well known in the art. The blowing agent and catalyst are each present in the know amount necessary to achieve the function of the component. Thus, the blowing agent is present in a minor amount sufficient to foam the reaction mixture to the desired density and the catalyst is present in a catalytic amount (i.e., an amount sufficient to catalyze the reaction to produce the polyurethane at a reasonable rate). The siloxane is present in a foam-stabilizing amount (i.e., in an amount sufficient to stabilize the foam). The siloxane is preferrably employed in an amount of from 0.2 to 5.0 parts by weight per 100 parts by weight of the polyol, polyisocyanate, catalyst and siloxane.

Conventional additives can be employed in minor amounts in producing polyurethane foams in accordance with the process of this invention if desired for specific purposes. Such additives include inhibitors (such as alpha-methyl styrene and alloocimene) and flame retardants (such as ("FYROL-6").

If desired, mixtures of the above-described starting materials (i.e., polyols, polyisocyanates, etc.) can be used in producing polyurethane foams in accordance with this invention.

In accordance with this invention, polyurethane foams are produced by the conventional procedures such as the one-step or one-shot technique wherein all of the reactants are reacted simultaneously with the foaming operation. The foaming and the urethane-forming reaction in the one-step technique occur without the application of external heat. Thereafter, the foam can be heated (postcured) at 150°C. to 212°F. to eliminate any surface tackiness if desired. Preferred novel siloxanes and premixture containing the novel siloxanes are of low viscosity and do not present particular problems when pumped into mixing headings in the technique conventionally used in the one-shot process. It is often convenient to prepare premixtures containing the hydroxyalkylsiloxane, the blowing agent and the polyol. Such premixtures can also contain the catalysts and/or other additives.

The rigid polyurethane foams produced in accordance with this invention can be used for the same purposes as conventional rigid polyether polyurethane foams (e.g., they can be used as thermal insulating materials in buildings and in refrigerators).

The hydroxyalkenylsiloxanes of this invention are also useful as lubricants for textile fibers, emulsifiers and wetting agents.

In the above formulas, the symbols representing the numbers and types of groups need not have the same meaning at each occurrence throughout the composition. For example, some of the groups represented by formula (II) above can be dimethylsiloxane ($Me_2SiO$) while other of such groups can be triethylsiloxane groups ($[C_2H_5]_3SiO_{0.5}$).

Other hydroxy-organosiloxane rigid polyurethane foam stabilizers are disclosed in U.S. Pat. application No. 319,788, filed concurrently herewith in the names of G. M. Omietanski, H. D. Furbee and V. T. Chuang entitled "Hydroxybicyclosiloxane Rigid Urethane Foam Stabilizers" and in U.S. Pat. application Ser. No. 319,528, filed concurrently herewith in the names of G. M. Omietanski and V. T. Chuang, entitled "Hydroxyalkylsiloxane Rigid Urethane Foam Stabilizers" now U.S. Pat. No. 3,879,433.

The following Examples illustrate the present invention.

In the following Examples, the abbreviations and symbols used have the indicated meanings:

| | |
|---|---|
| cc | cubic centimeters |
| cstks | viscosity in centistokes at 25°C. |
| Et | ethyl |
| "FYROL-6" | Diethyl-bis(2-hydroxyethyl)amino methylphosphonate |
| g. | grams |
| gal. | gallon |
| I.R. | infra red |
| lbs. | pounds |
| Me | methyl |
| min. | minute |
| ml. | milliliter |
| MW | molecular weight |
| NMR | Nuclear Magnetic Resonance |
| % | percent |
| "PAPI" | A polymeric polyisocyanate having the average formula: |

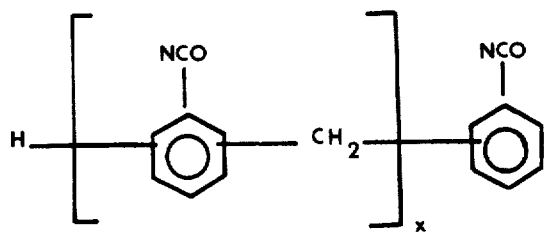

where x has an average value of 1.7

| | |
|---|---|
| Polyol I | A polypropylene oxide triol having a hydroxyl number of 450 produced by reacting sucrose with propylene oxide |
| ppm | parts by weight per million parts by weight |
| psig | pounds per square inch gauge pressure |
| sparge | Denotes passing a gas (e.g., nitrogen) through the liquid. |
| TMBDA | N,N,N',N'-tetramethyl-1,3-butanediamine. |
| "UCON-11" | trichloromonofluoromethane. |

HYDROSILOXANE PREPARATION

The following procedure is illustrative of a method that can be employed in making the hydrosiloxane reactants useful in producing the hydroxyalkenylsiloxanes of this invention. A solution of 0.0218 moles of a hydrosiloxane having the nominal formula $Me_3SiO(MeHSiO)_{40}SiMe_3$ (55.1 g, 354 cc/g SiH), a mixture of hexamethylcyclotrisiloxane and octamethylcyclotetrasiloxane (63.6 g) and 0.193 moles of hexamethyldisiloxane (31.4 g, 99.8 percent) were reacted in the presence of 3.0 g sulfuric acid (reagent grade) for 4 hours. This solution was then neutralized with sodium bicarbonate and filtered to give a water white clear equilibrated filtrate with a "nominal" formula of $Me_3SiO(Me_2SiO)_4$-$(MeHSiO)_4$-$SiMe_3$, a viscosity of 4.2 centistokes and a silanic hydrogen content of 129 cc/g. The above described reactions were carried out in a 500 ml, three-necked round bottom Morton flask equipped with a stirrer and two glass stoppers. The above "nominal" formula for this hydrosiloxane is the theoretical formula calculated on the basis of complete reaction of the siloxane starting materials. In this instance, the "nominal" formula is in agreement with the experimentally measured silanic hydrogen content of the hydrosiloxane. In the case of those of the hydrosiloxanes described below where the experimentally measured silanic hydrogen contents did not agree with the "nominal" formulas, the "nominal" formulas were corrected to agree with the silanic hydrogen measurement and the corrected formulas appear below.

CATALYST SOLUTIONS

The chloroplatinic acid used in producing the hydroxyalkenylsiloxanes described below was employed in the form of a solvent solution. The solution contained 3.3 or 10 parts by weight of chloroplatinic acid hexahydrate and 96.7 or 90 parts by weight of a mixture of solvents. The mixture of solvents consisted of 90 weight percent of the dimethyl ether of ethylene glycol and 10 weight percent of ethanol.

EXAMPLE I

A solution of 0.308 moles of 3-hydroxy-3-methyl-1-butyne (dimethyl propargyl alcohol) (26.3 g, 98.3 percent purity, pH of 7.0) and a hydrosiloxane having the average formula $Me_3SiO(Me_2SiO)_{5.2}$-$(MeHSiO)_{7.6}SiMe_3$ (0.28 equivalents of SiH, 36.3 g, 173 cc/g SiH, 7.2 cstks) were reacted in the presence of 0.08 cc of 10 wt.-percent chloroplatinic acid solution (100 parts by weight of platinum per million parts by weight of reactants) to give an adduct of the average formula of $Me_3SiO(Me_2SiO)_{5.2}[HOCMe_2CH=CH\text{-}SiMeO]_{7.6}SiMe_3$ and a viscosity of 30,898 cstks. The reaction was carried out in a 250 ml, three-necked round bottom flask fitted with a stirrer, thermometer, Dean-Stark trap, sparge tube and a condenser. The solution, under a nitrogen sparge was mixed and heated to 60°C and catalyzed. Further heating to 91°C resulted in an exotherm which was controlled. Additional heating at 100°C was maintained until the hydrosilation was completed (as evidenced by the absence of hydrogen in the silicon hydride-alcoholic potassium hydroxide fermentation tube test). The solution was then lites stripped at 100°C under a nitrogen sparge. Total preparation time was 22.5 hours.

EXAMPLE II

Employing the procedure used in Example I 0.272 moles of the same acetylenic alcohol (23.3 g, 98.3 percent purity, pH of 7.0) was reacted with a hydrosiloxane with nominal formula $Me_3SiO(Me_2SiO)_4$.$MeHSiO)_4SiMe_3$ (0.259 equivalents of SiH, 45.0 g, 129 cc/g SiH, 4.2 cstks) in the presence of 1.12 cc of 3.3 wt-percent chloroplatinic acid solution (200 parts by weight of platinum per million parts by weight of reactants) to give an adduct with the average formula $Me_3SiO(Me_2SiO)_4[HOCMe_2CH=CHSiMeO]_4SiMe_3$ and a viscosity of 1,661 cstks. I.R. analysis indicated the presence of a hydroxyl functionality at 3.0 microns which is consistent with the above formula.

EXAMPLE III

Using the procedure described in Example I, 0.218 moles of $HC \equiv CCMe_2OH$ (18.6 g, 98.3 wt-percent, pH of 7.0) was added to $Me_3SiO(Me_2SiO)_4(MeHSiO)_{2.8}SiMe_3$ (0.211 equivalents of SiH, 43.8 g, 102 cc/g SiH, 4.2 cstks) with 0.08 cc of 10 wt-percent chloroplatinic acid solution (100 parts by weight of platinum per million parts by weight of reactants) present. The resultant product mainly had an average formula of $Me_3SiO(Me_2SIO)_4[HOCMe_2-CH=CHSiMeO]_{2.8}SiMe_3$ and a viscosity of 405 cstks. The presence of OH absorption at 3.0 microns, as determined by I.R. analysis is consistent with the above average formula.

EXAMPLE IV

For purposes of comparison and using the procedure described in Example I, 0.219 moles of HC CCMe$_2$OH (18.7 g, 98.3% purity, pH of 7.0) was added to $Me_3SiO(MeHSiO)SiMe_3$ (0.173 equivalents of SiH, 38.8 g, 98.9% purity) in the presence of 0.14 cc of 10 wt-percent chloroplatinic acid solution (100 parts by weight of platinum per million parts by weight of reactants). This addition resulted mainly in the following adduct: $Me_3SiO[HOCMe_2CH=CHSiMeO]SiMe_3$.NMR analysis confirmed that the product had a ratio of two terminal adduct (trans) to one internal adduct and also indicated that no side reaction (i.e., SiH+COH) had occurred. The viscosity of this adduct was 11.8 cstks and IR analysis indicated the presence of OH absorption at 3.0 microns which is also consistent with the above formula.

EXAMPLE V

Employing the procedure described in Example I, 0.196 moles of 3-hydroxy-3-methyl-1-pentyne (20.0 g, 99.9% purity, pH of 7.0) was reacted with a hydrosiloxane having the nominal formula $Me_3SiO-(Me_2SiO)_4$-$(MeHSiO)_{2.8}SiMe_3$ (0.194 equivalents of SiH, 42.6 g, 102 cc/g SiH, 4.2 cstks) in the presence of 0.05 cc of a 3.3 wt-percent chloroplatinic acid solution (10 parts by weight of platinum per million parts by weight of reactants) as the catalyst to give a product which has the average formula of $Me_3SiO(Me_2SiO)_4[HOCMeEtCH=CHSiMeO]_{2.8}SiMe_3$ and a viscosity of 262 cstks. The presence of OH absorption at 3.0 microns, as determined by I.R. analysis is consistent with the average structural formula.

EXAMPLE VI

For purposes of comparison and employing the procedure described in Example I, 0.157 moles of 3-hydroxy-3-methyl-1-butyne (13.4 g, 98.3% purity pH of 7.0) was added to $Me_3SiOSiMe_2H$ (0.149 equivalents of SiH, 24.0 g, 91.6%) in the presence of 0.03 cc of a 3.3 wt-percent chloroplatinic acid solution (10 parts by weight of platinum per million parts by weight of reactants). This addition resulted in an adduct with the formula: $Me_3SiO[SiMe_2CH=CHMe_2COH]$. The presence of OH absorption at 3.0 microns as determined by I.R. analysis is consistent with the nominal formula.

The structure and properties of the hydroxyalkenylsiloxanes produced as described in Examples I to VI above are tabulated in Table I below.

TABLE I

HYDROXYALENKYLSILOXANE STRUCTURE AND PROPERTIES

| Product From Example | Product Structure (1) | Wt.-% "Siloxane" (2) | "Siloxane" Mol. Wt. (2) | Product Viscosity (cstks.) |
|---|---|---|---|---|
| I | MD$_{5.2}$D'$_{7.6}$M | 61 | 995 | 30,898 |
| II | MD$_4$D'$_4$M | 67 | 694 | 1,661 |
| III | MD$_4$D'$_{2.8}$M | 72 | 623 | 405 |
| IV (3) | MD'M | 72 | 221 | 11.8 |
| V | MD$_4$D''$_{2.8}$M | 69 | 623 | 262 |
| VI (3) | MM' | 63 | 147 | — |
| (4) | — | 34 | 1,445 | 350 |

Footnotes to Table I
(1) M denotes Me$_3$SiO$_{0.5}$
    D denotes Me$_2$SiO
    D' denotes HOCMe$_2$CH=CH SiMeO
    D" denotes HOCMeEtCH=CHSiMeO
    M' denotes HOCMe$_2$CH=CHSiMe$_2$O$_{0.5}$
(2) "Siloxane" denotes the portion of the product exclusive of the hydroxyalkenyl (i.e., the HOCMe$_2$CH=CH— and HOCMeEtCH=CH— group).
(3) Not a hydroxyalkenylsiloxane of this invention. Presented only for purposes of comparison.
(4) A commercially available siloxane-polyoxyalkylene block copolymer rigid polyether polyurethane foam stabilizer. Not a hydroxyalkenylsiloxane of this invention. Presented only for purposes of comparison.

EXAMPLE VII

The siloxanes produced as described in Examples I to VI above were used in producing polyurethane foams using the formulation and foaming procedure described below.

| Material | Formulation Parts by Weight |
|---|---|
| Polyol I | 70.0 |
| "FYROL-6" | 30.0 |
| "UCON-11" | 50.0 |
| TMBDA | 1.5 |
| Hydroxyalkenylsiloxane | 0.2 or 0.4 |
| "PAPI" (Index 105) | 110.0 |

FOAMING PROCEDURE

A cleaned and waxed mold was heated to 212°F. and any excess wax was removed with a clean cloth. A premixture was formed containing the "FYROL-6," Polyol I, TMBDA and "UCON 11." The premixture was thoroughly mixed until completely homogeneous and any "UCON 11" that volatilized during mixing was replaced. The mold is cooled to about 120°F. The siloxane is added to the premixture and the premixture is again mixed for 10 seconds. Then the "PAPI" is added to the premixture and the resulting formulation is mixed for 8 seconds. The formulation is introduced into the mold which is then closed. The temperature of the mold is maintained at 115° to 125°F. for 5 minutes. Then the mold is placed into a 212°F. oven for 5 minutes. The cured foam is then removed from the mold. A slice is cut from the center of the foam and the number of cells per linear inch in the middle of the slice is measured. The latter measurement is an index of the fineness of the cell structure. A foam having fewer than 26 cells per inch is regarded as unsatisfactory ("coarse"). The "Rise" or height of the foam is measured. In view of the fact that the formulation used to produce the foam is viscous, a portion thereof sticks to the walls of the container in which the formulation is formed when the bulk of the formulation is introduced into the mold. Accordingly, the foam is weighed and the measured rise is corrected to allow for the amount of the formulation retained in the container by using the following formula:

$$\text{Corrected Rise} = \left[10 \times \frac{\text{formulation weight}}{\text{foam weight}} - 10\right] + \left[\text{Measured Rise}\right]$$

Corrected Rise values are reported below. The Rise of a foam is roughly proportional to the potency of the foam stabilizer used to produce the foam.

PREMIXTURE COMPATIBILITY TEST

A mixture is formed containing the following materials:

```
840 grams Polyol I
360 grams "FYROL-6"
 18 grams TMBDA
600 grams "UCON-11"
```

The mixture is stirred at moderate speed with an air motor equipped with a 2 inch propeller. Any "UCON-11" that evaporates during the mixing is replaced by adding more "UCON-11" to the mixture. A 75.8 gram sample of the mixture so formed is added to a jar and then 0.5 cubic centimeters of a hydroxyalkenylsiloxane is added to the jar to form a premixture. The premixture is maintained at a temperature below 23°C to minimize loss of "UCON-11" by volatilization. The premixture is stirred with a spatula until well mixed and is then observed visually for clarity or opaqueness.

The results of the above foam preparations are shown in Table II below:

TABLE II

| Product From Example | TEST RESULTS Foam Test | | | |
|---|---|---|---|---|
| | Parts by Weight | Rise (In.) | Cells Per In. | Premixture Compatibility Test |
| I | 0.4 | 17.7 | 40 | Clear |
| | 0.2 | 17.0 | 38 | |
| II | 0.4 | 20.3 | 44 | Clear |
| | 0.2 | 16.7 | 38 | |
| III | 0.4 | 17.5 | 32 | Clear |
| | 0.2 | 16.3 | Coarse | |
| IV (a) | 0.4 | No foam produced | | Clear |
| | 0.2 | | | |
| V | 0.4 | 18.0 | 42 | Clear |
| | 0.2 | 17.8 | 32 | |
| VI (a) | 0.4 | 1.4 | Coarse | |

TABLE II-continued

| Product From Example | TEST RESULTS Foam Test | | | |
|---|---|---|---|---|
| | Parts by Weight | Rise (In.) | Cells Per In. | Premixture Compatibility Test |
| (b) | 0.2 | 18 | 35 | Clear |

Footnotes to Table II
(a) Not a hydroxyalkenylsiloxane of this invention. Presented only for purposes of comparison.
(b) See footnote (4) to Table I above.

The poor foams obtained using the hydroxyalkenylsiloxanes of Examples IV and VI illustrate the importance of the siloxane molecular weight limitations that characterize the hydroxyalkylsiloxanes of this invention. The siloxanes of Examples IV and VI had siloxane molecular weights of less than 250.

In the above Examples, the formula of the principal (terminal or trans) adduct product is shown. Some of the isomeric (internal) adduct was also produced in each case.

What is claimed is:

1. A method for producing a rigid polyurethane foam by reacting and foaming a foam formulation comprising (a) a polyether containing at least two hydroxyl groups and having a hydroxyl number from about 200 to about 1000, (b) an organic polyisocyanate, (c) a catalyst for the reaction of (a) and (b) to produce the polyurethane, (d) a blowing agent and (e) a hydroxyalkenylsiloxane consisting essentially of (A) at least one hydroxyalkenylsiloxane unit having the formula:

wherein R is a divalent hydrocarbon group free of aliphatic carbon to carbon multiple bonds, R' is an arylene group, a cycloalkylene group that has no hydrogen bonded to the carbon atom attached to the $C_2H_2$ group and that is free of aliphatic carbon to carbon multiple bonds or a divalent-$CR''_2$-group, R'' and R° are each monovalent hydrocarbon groups free of aliphatic carbon to carbon multiple bonds and having from 1 to 10 inclusive carbon atoms, $C_2H_2$ is a -CH=CH- or a $$-C=CH_2$$

group, each hydroxyalkenylsiloxane group has no more than 20 carbon atoms, a has a value of 0 or 1, b has a value of 1, 2 or 3, c has a value of 0, 1 or 2, and (b+c) has a value of 1, 2 or 3; and (B) at least three hydrocarbylsiloxane units represented by the formula:

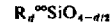

wherein R° is a monovalent hydrocarbon group free of aliphatic carbon to carbon multiple bonds and having from 1 to 10 inclusive carbon atoms and d has a value of 1, 2 or 3, the molecular weight of the siloxane portion of the hydroxyalkenylsiloxane being from about 250 to about 1300 inclusive, and, when dihydrocarbylsiloxane units $R_2^{\infty}SiO$ units) are present, the ratio of hydroxyalkenylsiloxane units to dihydrocarbylsiloxane units is at least 0.5 to 1.0.

2. A method as claimed in claim 1 wherein the hydroxyalkenylsiloxane is represented by the average formula:

$$\underset{|}{HOCR_2'''C_2H_2-}$$
$$Me_3SiO(MeSiO)_x(Me_2SiO)_ySiMe_3$$

wherein R''' is a methyl or ethyl group, Me is a methyl group, $x$ has a value from 1 to 8 inclusive, $y$ has a value from 1 to 6 inclusive, the molecular weight of the hydroxyalkenylsiloxane, exclusive of the hydroxyalkenyl groups, is from about 300 to about 1000 inclusive and $x:y$ is at least 0.5:1.

3. A premixture suitable for use in the method of claim 1 which premixture consists essentially of a hydroxyalkenylsiloxane, a blowing agent and a polyol, all as defined in claim 1.

* * * * *

UNITED STATES PATENT OFFICE
CERTIFICATE OF CORRECTION

Patent No. 3,933,695              Dated January 20, 1976

Inventor(s) G. M. Omietanski et al

It is certified that error appears in the above-identified patent and that said Letters Patent are hereby corrected as shown below:

Col. 1, line 16, after "amounts", "of the materials" should read "of the starting materials".

Col. 6, line 36 "know" should be "known".

Col. 6, line 65 "150°C." should be "150°F.".

Col. 9, line 41 "HC CCMe$_2$OH" should be "HC≡CCMe$_2$OH".

Signed and Sealed this eighteenth Day of May 1976

[SEAL]

Attest:

RUTH C. MASON
*Attesting Officer*

C. MARSHALL DANN
*Commissioner of Patents and Trademarks*